(12) United States Patent
El Hatu

(10) Patent No.: US 6,610,027 B1
(45) Date of Patent: Aug. 26, 2003

(54) HEMODIALYSIS

(75) Inventor: Mohamed Kaled Mohamed El Hatu, 52 Tayaran Street, Nasr City, Nasr (EG)

(73) Assignee: Mohamed Kaled Mohamed El Hatu, Nasr (EG)

( * ) Notice: Subject to any disclaimer, the term of this patent is extended or adjusted under 35 U.S.C. 154(b) by 427 days.

(21) Appl. No.: 09/570,782

(22) Filed: Aug. 17, 2000

(51) Int. Cl.[7] .............................................. A61M 31/00
(52) U.S. Cl. ........................................ 604/65; 604/4.01
(58) Field of Search .............................. 604/4.01, 6.06, 604/6.09, 6.1, 6.11, 27, 30, 65–67; 600/573; 210/645, 646, 805

(56) References Cited

U.S. PATENT DOCUMENTS

| | | | | |
|---|---|---|---|---|
| 4,610,781 A | * | 9/1986 | Bilstad et al. ......... | 210/321.65 |
| 4,827,430 A | * | 5/1989 | Aid et al. ............... | 210/321.71 |
| 5,725,776 A | * | 3/1998 | Kenley et al. .............. | 210/645 |
| 6,221,040 B1 | * | 4/2001 | Kleinekofort ............... | 604/4.01 |
| 6,258,027 B1 | * | 7/2001 | Sternby ....................... | 210/646 |

* cited by examiner

Primary Examiner—Timothy L. Maust

(57) ABSTRACT

Accelerated hemodialysis is a novel method of extracorporeal blood tratment in which a high blood flow rate through the filter and a low blood flow to and from the patient is achieved by using accelerated hemodialysis lines composed of arterial line connecting blood from the patient to the filter, venous line connecting blood from the filter to the patient and a recirculation line carrying part of the blood from the venous line to the arterial line and is controlled by using 2 adjustable blood pumps or one blood pump and an adjustable valve situated at suitable sites of the circuit, with an optional safety program comparing the blood flow rates in different parts of the blood lines and the ultrafilteration rate to ensure safe operation.

3 Claims, 11 Drawing Sheets

| Set Δ p Fp/Ff | 0 | 1-100 | 101-200 | 201-300 | 301-400 | 401-500 | 501-600 |
|---|---|---|---|---|---|---|---|
| 100% | 0 | 0 | 0 | 0 | 0 | 0 | 0 |
| 95% | 1 | 1 | 1 | 1 | 1 | 1 | 1 |
| 90% | 3 | 2 | 2 | 2 | 2 | 2 | 1 |
| 85% | 4 | 4 | 3 | 3 | 3 | 2 | 1 |
| 80% | 5 | 5 | 4 | 4 | 3 | 3 | 2 |
| 75% | 6 | 6 | 5 | 5 | 4 | 4 | 3 |
| 70% | 7 | 7 | 5 | 5 | 4 | 4 | 4 |
| 65% | 8 | 8 | 8 | 7 | 7 | 6 | 5 |
| 60% | 9 | 8 | 8 | 7 | 6 | 5 | 4 |
| 55% | 9 | 9 | 8 | 8 | 7 | 6 | 5 |
| 50% | 10 | 9 | 8 | 8 | 7 | 6 | 6 |
| 45% | - | 10 | 9 | 9 | 8 | 7 | 6 |
| 40% | - | - | 10 | 10 | 9 | 8 | 7 |
| 35% | - | - | - | 10 | 10 | 9 | 8 |
| 30% | - | - | - | - | 10 | 9 | 8 |
| 25% | - | - | - | - | - | 10 | 9 |
| 20% | - | - | - | - | - | - | 10 |
| 15% | - | - | - | - | - | - | - |

HEMODIALYSIS

CROSS REFERENCE TO RELATED APPLICANT & CLINICAL RESEARCH

"Accelerated hemodialysis: a new safe & simple method of a high filter low patient blood flow rate hemodialysis" Elhatw Mohamad K. M. RENAL FAILURE (21) 5 1999.

presented as a talk in the first African Pediatric Nephrology Association meeting in Cairo, March 2000.

presented as a Poster in the 34 European Pediatric Nephrology Association meeting in Helsinki June 2000.

"Accelerated hemodialysis connections' Egyptian patent office filed on May 20, 1998 No 547.5.1998 Approved, Under print. Applicant: Dr. Mohamed Khaled Mohamed El Hatw.

"The calibrated recirculation valve' Egyptian patent office filed on Aug. 5, 2000 No 1008 8 2000 Applicant: Dr. Mohamed Khaled Mohamed El Hatw.

BACKGROUND OF THE INVENTION

1. The Old Art

Hemodialysis is done by passing the patient's blood in semiperniable capillaries or plates impregnated in a physiological solution where toxins pass to the refreshing solution & is discarded.

In the traditional double needle hemodialysis the blood passes in different parts of the circuit by a constant speed that is controlled by the speed of the blood pump.

An average speed is selected in the normal situations whereas a slow speed is selected in patients with cardiovascular instability & in children while a rapid speed is selected in heparin free dialysis.

2. Defects in the Old Art

With slow blood flow rate the blood is liable for clotting as its movement is a major factor in preventing blood clotting.

With high filter blood flow rate the patient is liable for cardiovascular instability & heart failure as the dialysis is considered an extra effort load on the heart.

To conclude the high speed is hazardous to the patient while the slow speed is hazardous to the blood & the filter.

BREIF SUMMARY OF THE INVENTION

Accelerated hemodialysis lines are new lines of hemodialysis which allow controlled partial recirculation of blood from the venous to the arterial line leading to acceleration of blood flow through the filter without increase of the actual patient blood flow.

The regulator of blood flow in the pump controlled accelerated hemodialysis lines is the additional pump while in the pressure controlled lines the regulator is a valve which is either a blood flow rate controlled valve (Doppler flow meter controlled) or a blood lines pressure controlled valve (The calibrated recirculation valve).

The calibrated recirculation valve is a valve used to control the diameter of the recirculation segment in the pressure controlled acceleration hemodialysis lines by using specific calibrations for each particular line, the calibrated recirculation valve allows DIRECT adjustment of the patient blood flow.

The valve may be operated manually with the calibration inbuilt in the valve or supplied in separate graphs or it may work automatically under control of a the computer program prefed with these calibrations This program may be inbuilt in the hemodialysis machine or supplied in a separate computer.

Any of the usual forms of externally compressing or internally obstructing valves can be used. The line kinking valve is a valve that externally control the diameter of flexible lines by manual or automatic controlled kinking of the lines.

Figure 1:
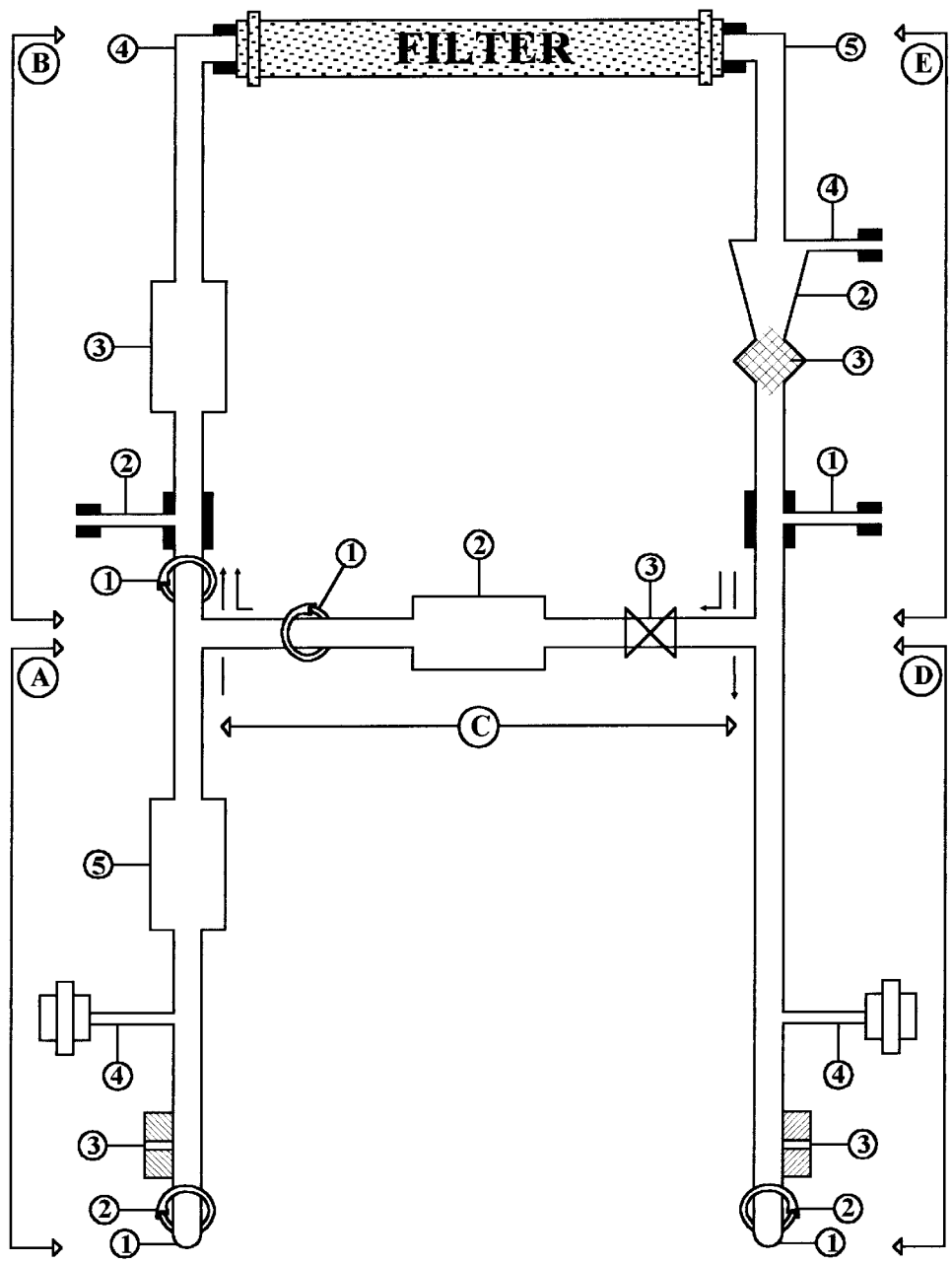
FIG. 1: The principle components of the accelerated hemodialysis line The accelerated hemodialysis line is composed of 5 segments The patient segment of the arterial line Fistula needle end Clamp. Injection site. Arterial blood pressure connection. Pump segment in Models (M-H-RP) (M-H-PF) (M-U-P). The filter segment of the arterial line Clamp in models (M-H-RP) (V-H). Heparin injection connection. Pump segment in Models (M-H-PF) (M-H-RF) (V-H). Filter end. Recirculation segment Clamp Pump segment in Models (M-H-RP) (M-H-RF) (M-U-R). Valve in models (V-H)(V-U). The patient segment of the venous line Fistula needle end Clamp Injection site Venous blood pressure connection. The filter segment of the venous line Fluid injection connection Air trapping chamber+blood clot filter+ air exit Filter end.

(12) the pressure graduation of the circular plate (13) Arrow 2 (14) central hole of the circular plate (15) C shaped hole of the circular plate(16) the pressing disc (17) the central hole of the pressing disc (18) the sickle shaped hole of the pressing disc (19) the shoulders of the pressing disc (20) the central axis (21) the axis sheath (22) the anterior screw (23) the posterior screw (24).

Figure 8:
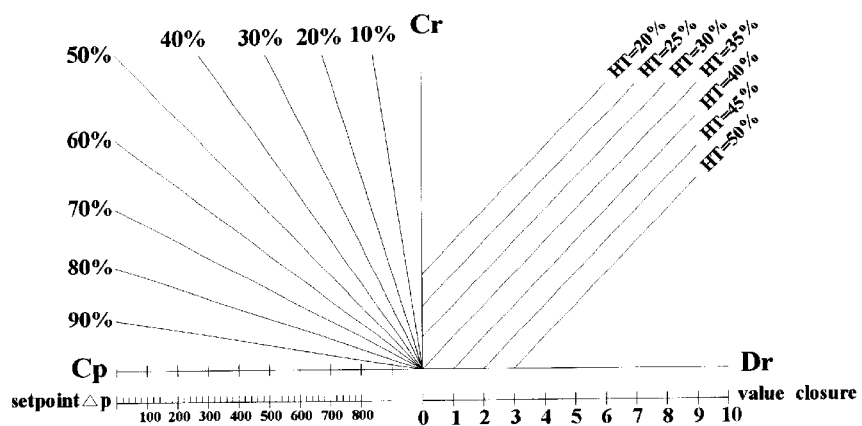

FIG. 8; Graphs & tables associating the manual precalibrated valve A—A diagrammatic graph for a particular type of accelerated hemodialysis line showing the linear relation between the following three parameters * The set point pressure gradient $\Delta p$ of the patient as an index of Cp.* The degree of closure of the valve & corresponding recirculation diameter (Dr) & the hematocrite (Ht) of the patient as an index of Cr.* The target ratio of patient/filter blood flow rates (Fp/Ff) To adjust the valve, measure The set point pressure gradient $\Delta p$ of the patient as an index of Cp & represent on the right X axis, draw a vertical line to meet the target Fp/Ff then a horizontal line to meet Cp at the Y axis then extend the horizontal line to meet the hematocrite & draw a vertical line to meet the target Dr on the right X axis. B-A diagrammatic table for a particular type of accelerated hemodialysis line showing the relation between the three prementioned parameters. For simplicity the hematocrite was not included.

Figure 9:
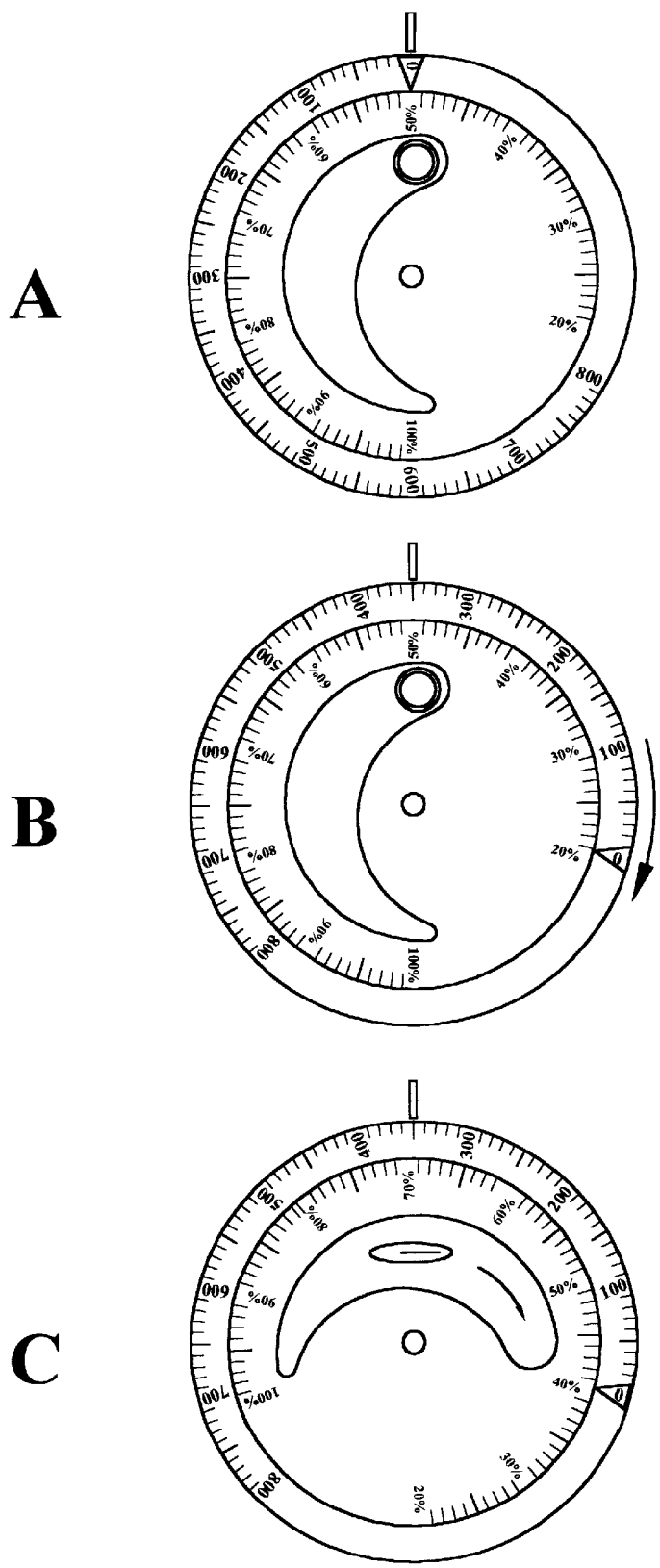

FIG. 9; The automatic recirculation valve with inbuilt computer program in the hemodialysis machine with an automatic kinking valve. the recirculation segment (1), the filter segment of the arterial line (2), the patient segment of the arterial line (3),the filter segment of the venous line (4) & the patient segment of the venous line (5), the bloodpump (6) & the valve (7). The hemodialysis machine (8) The computer program (9) The pressure monitors (10) The automatic kinking line valve is formed of An electric motor (11) with a spiral wheel (12). An arm (13) with a spiral groove to transfer motion from the motor to the joint of the acceleration segment holder. The acceleration segment holder is formed of 2 limbs (14) with a central joint (15) & clips (16) to fix the line on its anterior surface. Each limb has a longitudinal hole (17) which allows its movement along a fixed screw(18). Movement of the joint will change the angle between the 2 limbs & the degree of bending & diameter of the acceleration segment.

Figure 10:
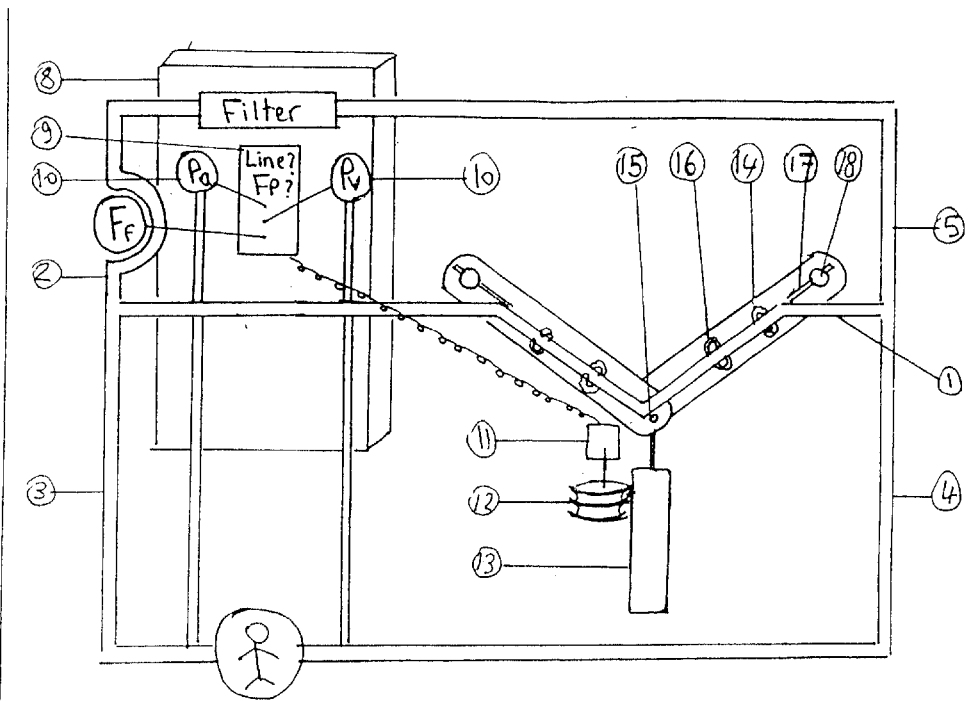

FIG. 10; The automatic recirculation valve with separate computer program with an automatic kinking valve. the Accelerated hemodialysis line (1), the blood pump (2) & the automatic kinking valve (3). The hemodialysis machine (4) The computer containing the computer program (5) The pressure monitors (6).

Figure 11:
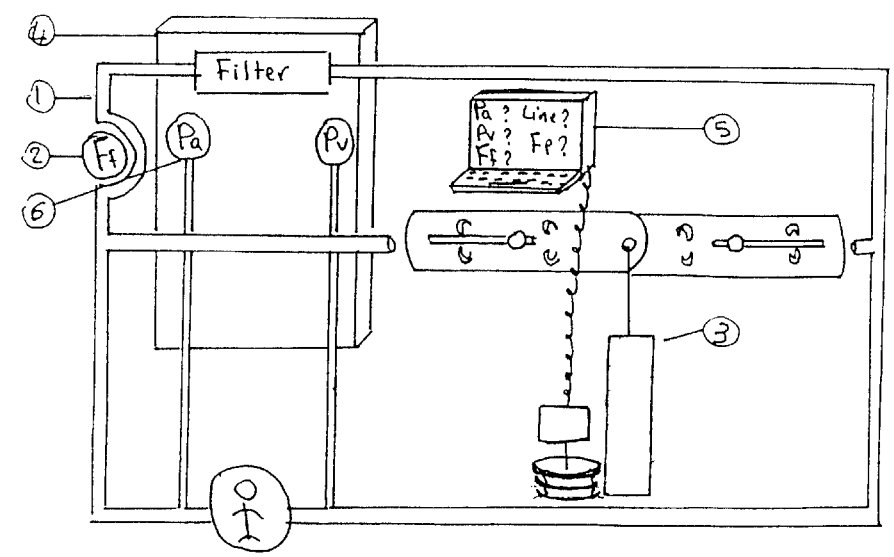

FIG. 11; How to use the self calibrated valve ? A—Identify the set point Fp/Ff of the lines. Open the valve completely. Rotate the circular plate so that arrow 1 faces the zero grade of the circular plate. Arrow 2 which corresponds to this zero grade will point to the set point Fp/Ff of the lines on the pressing disc. B—Adjusting the set point at the circular plate. Rotate the circular plate so that the arrow 1 (which identifies the recirculation line) points to the set point $\Delta p$ of the patient. Arrow 2 will point to the Fp/Ff ratio that will be achieved if the recirculation clamp is opened. C—Adjusting the pressing disc. Rotate the pressing disc so that the required patient/filter blood flow ratio marked on the pressing scale faces Arrow 2 at its new position. At this point the sickle hole will compress the recirculation line to achieve the required diameter.

Figure 12:
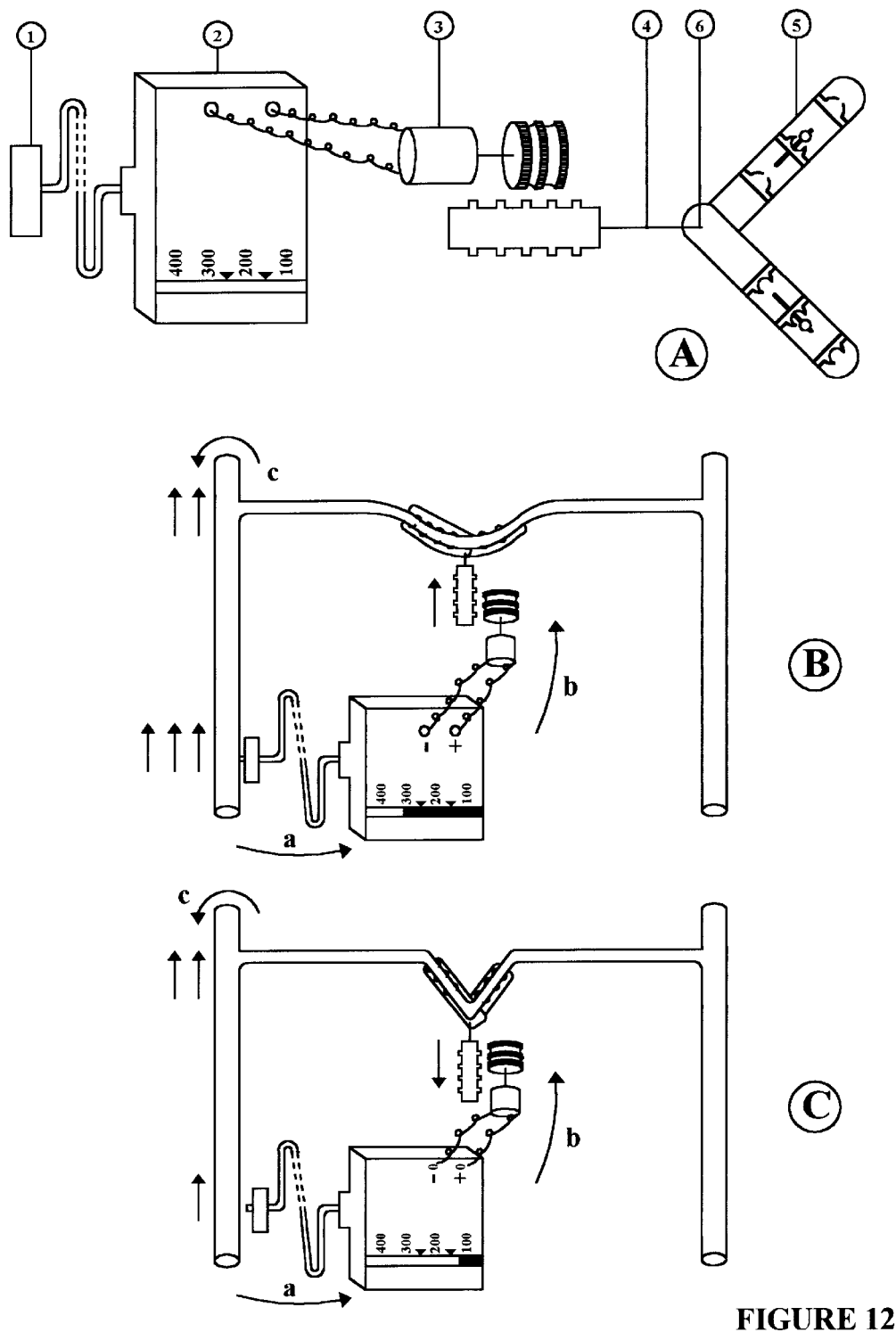

FIG. 12; The Doppler flow meter controlled valve system; A The components; Doppler Transducer (1) Control unit (2) A valve composed of An electric motor (3) An arm (4) Recirculation segment holder formed of 2 limbs (4) with a central joint (5) B (a) blood flow through the patient segment of the arterial line exceeds the upper limit. (b) the control unit will open the valve. (c) Blood flow will decrease through the recirculation segment and increase through the patient segment of the arterial line. C (a) blood flow through the patient segment of the arterial line decreases than the lower limit. (b) the control unit will close the valve. (c) Blood flow will increase through the recirculation segment and decrease through the patient segment of the arterial line.

Figure 13:
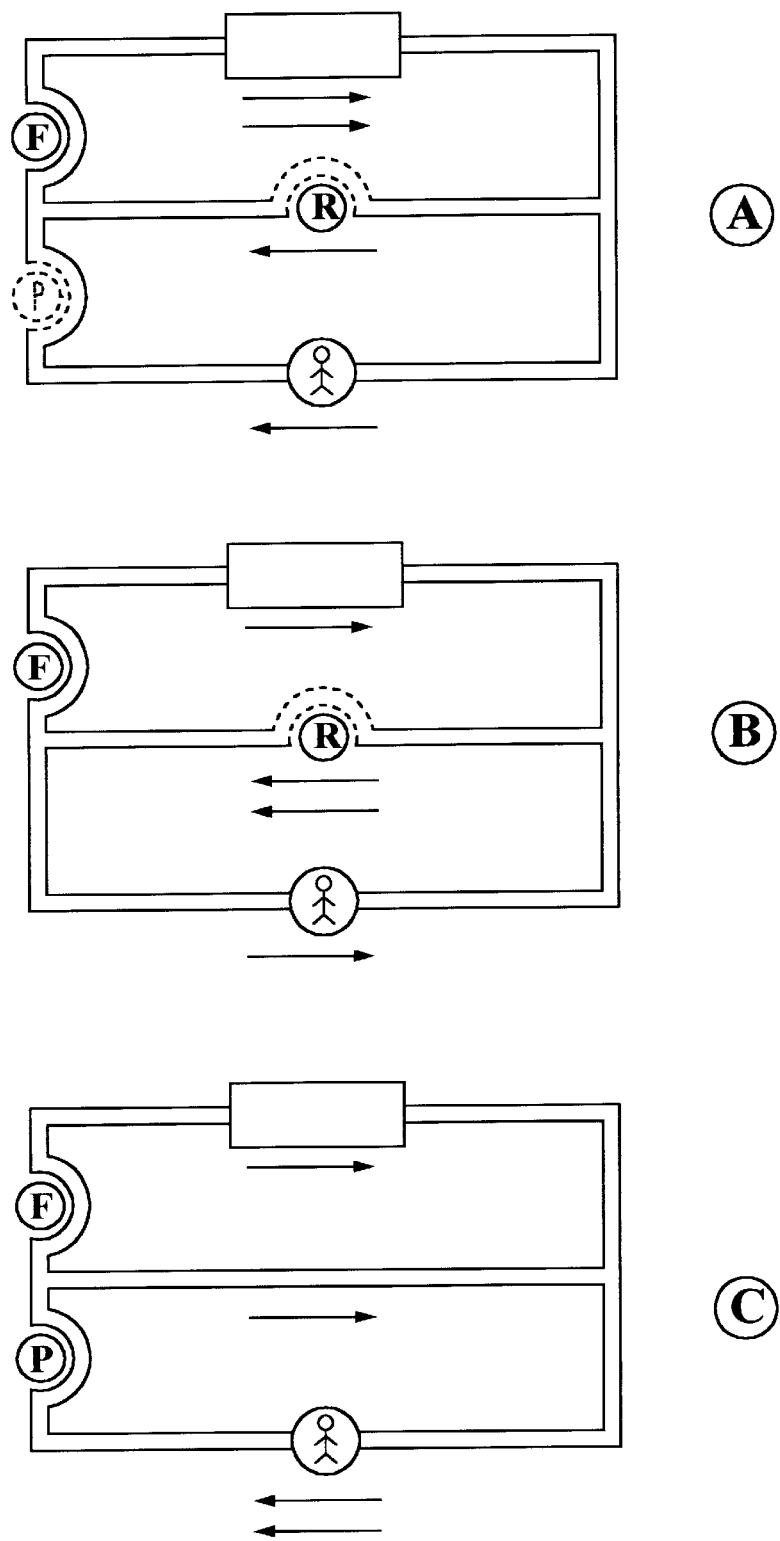

FIG. 13; The blood flow rate safety program; A The filter blood flow is higher than both the recirculation & the patient blood flow B the recirculation blood flow exceeds the filter blood flow leading to passage of blood in the patient in the reverse direction with the possibility of internal recirculation. C the patient blood flow exceeds the filter blood flow leading to passage of blood in the recirculation segment in the reverse direction with non beneficial external recirculation.

LIST OF SYMBOLS & DEFINITIONS
Models of the Accelerated Hemodialysis Lines
(V) valve controlled lines.
(M) Motor controlled lines.
(H) H shaped, Complete lines
(U) U shaped, complementary to double needle lines.
(P) With a blood pump on patient segment of the venous line.
(F) With a blood pump on filter segment of the venous line.
(R) With a blood pump on recirculation segment.
Algebraic Symbols
Ff=filter blood flow rate (passing in the filter)
Fp=patient blood flow rate (passing in the patient)
Fr=recirculation segment blood flow rate (passing in the recirculation line)
Pa=Pressure in the patient segment of the arterial line.
Pv=pressure in the patient segment of the venous line
$\Delta p$=Pressure gradient between the patient segments of the arterial & venous lines.
Dr=The recirculation segment diameter at the site of the valve.
C=Constant of the relation between the fluid flow rate & the square root of the pressure gradient.
Cp=The patient constant for blood flow rate in the patient lines
Cr=The recirculation segment constant for blood flow rate in this segment.
Definitions
Accelerated Hemodialysis
A new method of hemodialysis where controlled partial recirculation is allowed from the venous to the arterial line. This will allow higher filter &/or low patient blood flow in the same hemodialysis session.
Accelerated Hemodialysis Lines
Blood lines similar to the ordinary double needle blood lines with an additional recirculation segment. Blood flow in this segment is achieved by a valve in pressure controlled lines & by additional pump in pump controlled lines.
The Calibrated Recirculation Valves
Valves used in the pressure controlled accelerated hemodialysis lines to adjust the patient blood flow according to the pressure gradients (i.e. without the need of additional sensors).
The Graduated Calibrated Recirculation Valves
Valves which adjust the patient blood flow by restoring a pressure gradient measured at a known patient blood flow rate.
The Precalibrated Recirculation Valves
Valves which adjust the patient blood flow directly according to the target pressure gradient.
Set point $\Delta p$ of the patient the pressure gradient that derives a preset Pf in the patient lines (e.g, 100 ml/min in children or 200 ml/min in adults) when the recirculation line is closed.

It is a measure of the patient resistance Set point Fp/Ff of the lines=The ratio of patient/filter blood flow in the accelerated hemodialysis lines if the valve is completely open & the patient lines are directly connected (i.e, with minimal recirculation & patient lines resistance).

It is a measure of relative patient to recirculation line resistance.

DETAILED DESCRIPTION OF THE INVENTION

1—Accelerated Hemodialysis lines (seven models).
2—Regulator of the Accelerated Hemodialysis Lines (Pressure & flow sensors)
3—Safety Program.

I—THE ACCELERATED HEMODIALYSIS LINES

1—The Principle Components of the Accelerated Hemodialysis Line. (FIG. 1)

The Accelerated Hemodialysis Line is composed of 5 segments
The Patient Segment of the Arterial Line
  The segment between the arterial end of the patient & the recirculation segment. It contains:
Fistula needle end.
Clamp.
Injection site.
Arterial blood pressure connection.
Pump segment in Models (M-H-RP) (M-H-PF) (M-U-P).
The Filter Segment of the Arterial Line
  The segment between filter end of the arterial line & the recirculation segment. It contains:
Clamp in models (M-H-RP) (V-H).
Heparin injection connection.
Pump segment in Models (M-H-PF) (M-H-RF) (V-H). Filter end.
Recirculation Segment
  The segment connecting arterial and venous lines.
It contains:
Clamp.
Pump segment in Models (M-H-AP) (M-H-AF) (M-U-A).
Valve in models (V-H)(V-U).
The Patient Segment of the Venous Line
  The line between the patient end of the venous line & the recirculation segment.
It contains:
Fistula needle end.
Clamp.
Injection site.
Venous blood pressure connection.
The Filter Segment of the Venous Line
  The line between the venous end of the filter & the recirculation segment.
It contains:
Fluid injection connection.
Air trapping chamber+blood clot filter+air exit.
Filter end.

Figure 2:
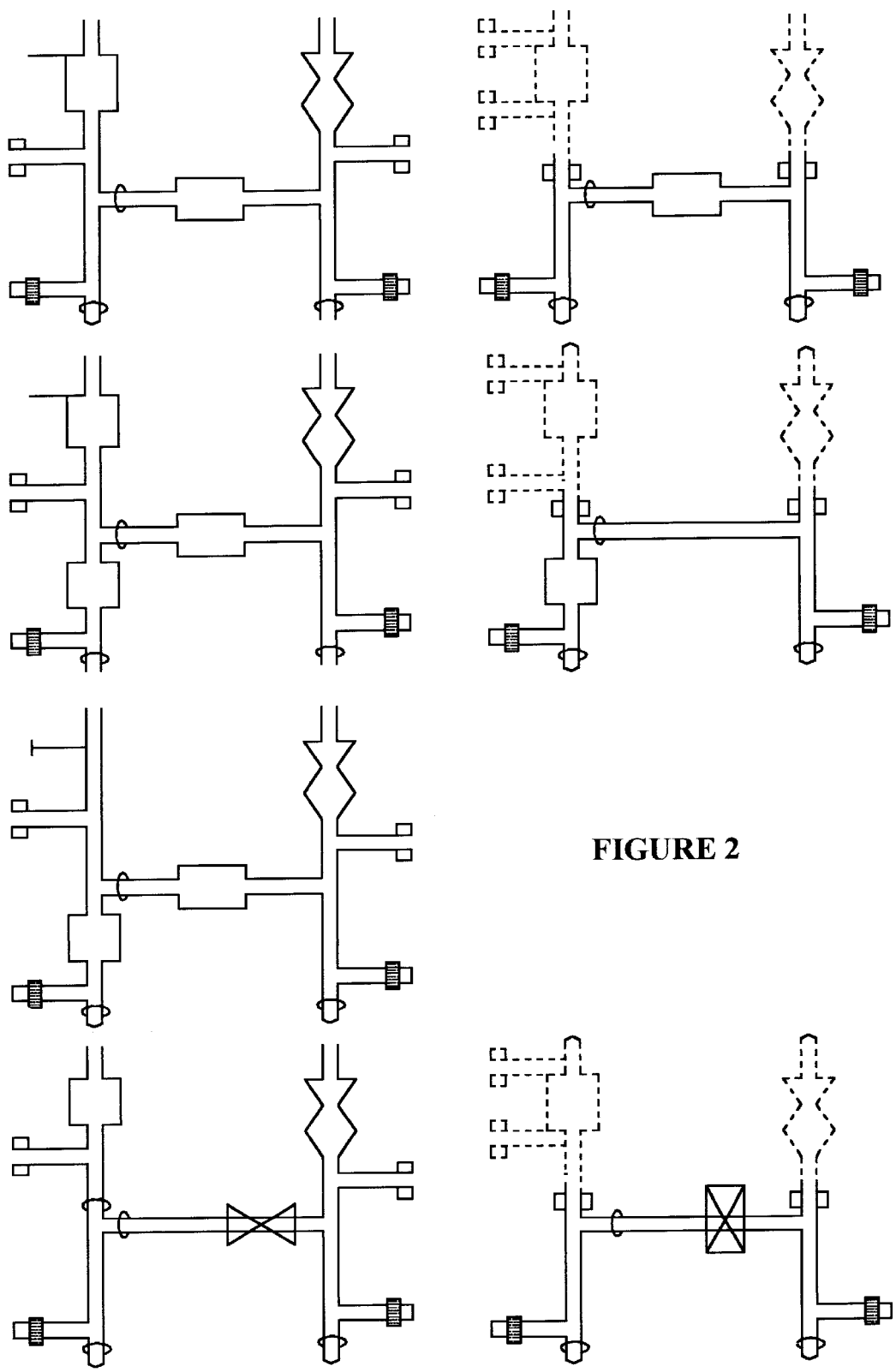
FIG. 2: Different models of Acceleration hemodialysis lines (M-H-RF) motor derived, complete with recirculation & filter pumps. (M-U-R) motor derived Complementary, With additional recirculation pump (M-H-PF) Motor derived, Complete, With patient & filter pumps (M-U-P) Motor derived, Complementary, With patient pump. (M-H-RP) Motor derived, Complete, With recirculation & patient pump A-H) Valve controlled Complete (V-U) Valve controlled coplementary.

The following modifications can be done:

Transfer heparin connection: from the patient segment of the arterial line to the filter segment of the arterial line
Transfer air-trapping chamber: from the filter segment of the venous line To the patient segment of the venous line
Transfer the valve: from the recirculation segment To the patient segment of the venous line 2—Models of Accelerated Hemodialysis Lines (FIG. 2)

There are 7 different models of accelerated hemodialysis lines according to.

1—Flow Regulator

|  | M | V |
|---|---|---|
| Regulator | Motor controlled with an additional blood pump. | Valve controlled with an additional blood flow valve. |
| Advantages | Accurate direct measurement of blood flow in the lines. | no need for an additional pump. Shorter lines. |
| dis-advantages | It needs an additional pump. Longer lines, to reach the machine. | Indirect measurement of blood. Flow according to blood pressure |

2—Components of the Lines

|  | H | U |
|---|---|---|
| Shape | H shaped | U shaped |
| Contents | Complete lines contains the 5 main segments. | complementary to double needle lines which are connected to work as filter segments |
| Advantages | Proportionate line lengths No unused connections | Can be used with all hemodialysis connections. Losses in the lines lengths. |
| dis-advantages | Needs manufacturing of different models to fit all types of hemodialysis machines. | Unused connections of the traditional lines |

3—Site of the Pump Segment

|  | P | F | R |
|---|---|---|---|
| Site of the Pump segment | Patient segment of the venous line. | Filter segment of the venous line. | Recirculation segment. |

Comparison between Different Models of Accelerated Hemodialysis Connections (A.H.D) Table (2)

|  | M-H-AF | M-U-A | M-H-PF | M-U-RP | M-H-RP | V-H | v-u |
|---|---|---|---|---|---|---|---|
| Dialysis pump segment | F | F | F | F | F | F | F |
| Recirculation pump | R | R | P | P | R | — | — |
| Blood flow Valve | — | — | — | — | — | R | R |
| Patient Blood Flow | P speed | P speed | F – R | F – R | P | Corresponding to pressure | |
| Filter Blood Flow | F speed | F | F | F | R + P | F | F |

3—How to Use Accelerated Hemodialysis Lines

1) Hemodialysis Machines and Options Used with Different Models of (A.H.D.) Lines. Table (3)

|  | M | V |
| --- | --- | --- |
| Main machine | All types of hemodialysis machines +Additional blood pump | All types of hemodialysis machines |
| Options | Safety program to Prevent F < R or F < P 1-Prevent disproportionate ultrafiltration with Patient flow | Accelerated hemodialysis Regulator for automatic adjustment of the valve according to patient Bl flow. |

Preparation of Lines

| model | Preparation |
| --- | --- |
| H | Ready for direct Use |
| U | Connect 2 traditional double needle hemodialysis (arterial and venous) Lines to works as filter segments of arterial & venous lines. |

3) Connection of Lines to the Patient & the Filter (FIG. 1)

Blood flows in arterial segments from the patient to the filter
Blood flows in Venous segments from the filter to the patient.
Blood flows in the recirculation segment from the venous to the arterial line.

Connect blood pump segment to the corresponding dialysis pump. (Principal) or acceleration (additional) pump as in table (4).

4) Priming

Connect the 2 ends to the bottom of a heparinized saline bottle either directly or through a Y connection.
Fill dialysis line & the filter first then fill the recirculation segment.
Any line can be closed with a clamp or by putting off the corresponding
Any line can be filled either with gravity or by putting on the corresponding pump.
Steps of priming of different models of accelerated hemodialysis Connections Table (4).

|  | 1- Priming of dialysis lines | 2- Priming of recirculation segment. |
| --- | --- | --- |
| M-H-RF | -Pump R off. | -Pump F off. |
| M-U-R | -Pump F on. | -Pump R on. |
| M-H-PF | -Recirculation segment closed with a clamp. | -Recirculation segment opened. |
| M-U-P | -Pumps F & P working with the Same speed. | -Pump F off. -Pump P on. |
| M-H-RP | -Pump R off. -Pump P on. | -Pump P off. -Connection P removed.. -Pump R on.. |
| V-H | -Recirculation segment closed with a Clamp. | -Pump F off. |
| V-U | -Pump F on.. | -Fill acceleration line e gravity by removing & descending one end. |

5) Adjustment of Pump(s) Speed in Different Models of Accelerated Hemodialysis Lines. Table (5)

| Model | Adjustment |
| --- | --- |
| M-H-RF M-U-R | -Put pump F on and increase its speed gradually to the target patient blood flow. -Put pump R on and increase speed of pumps F & R gradually, equally & alternatively till Target pump F speed is achieved. |
| M-H-PF M-U-P | -Put pumps P & F on and increase their speed gradually, equally and alternatively to the target patient blood flow. -Increase pump F speed to the target filter blood flow. |
| M-H-RP | -Put pump P on and increase its speed gradually to the target patient blood flow rate. -Put pump R on and increase its speed gradually until (A + P) is equal to the target filter blood flow. |
| V-H | Pressure guided noncalibrated manual valve method. |
| V-U | -Close the recirculation segment.. -Put pump F on and increase its speed to the target patient blood flow rate -Observe & record the pressure gradient between the venous & arterial lines corresponding to this blood flow. -Open the recirculation Valve & Observe the drop in the pressure gradient -Increase pump speed to the target filter blood flow rate. -Close the valve gradually till the original pressure gradient is restored. Doppler guided noncalibrated manual valve method. -Close the recirculation segment.. -Put pump F on and increase its speed to the target patient blood flow rate -Observe the blood flow rate by a Doppler flow meter on eithethe patient segments or the recirculation segment.. -Increase the pump speed to the target filter blood flow rate while opening the valve gradually to maintain the original Patient blood flow rate. Air bubble flow method. -Close the recirculation segment.. -Put pump F on and increase its speed to the target patient blood flow rate. -Observe & record the time needed for an injected air bubble to travel in a fixed distance in the patient segment of the arterial line corresponding to this blood flow. -Open the recirculation Valve. -Increase pump speed to the target filter blood flow rate. -Close the valve gradually with repeated injection of air bubbles till the original blood speed is restored. |

6) Evacuation of the Connections. (Table 6)

|  | 1-Patient and recirculation segments | 2-Filter & its segments |
|---|---|---|
| M-H-AF<br>M-U-A | 1-Reduce speed of pumps R & F alternatively equally and gradually till pump R stops.<br>2-Remove segment R from the pump and put pump F off<br>3-Transfer the arterial end to a Saline bottle to evacuate these lines by gravity | 4-Close recirculation segment.<br>5-Reduce pump F speed and<br>Put it on till saline reaches the air detector<br>6-Push the residual |
| M-H-PF<br>M-U-R | 1-Reduce speed of pump P & F alternatively equally and gradually pump P stops.<br>2-Remove segment P from the pump and put pump F off.<br>3-As before | 4-.As Before.<br>5-As Before.<br>6-As Before. |
| M-H-RP | 1-put pump A off<br>2-Remove p off and close one of the filter lines with a clamp.<br>3-As before. | 4-As before<br>5-Reduce pump p speed and put it on till saline reaches the air detector<br>6-As before.. |
| V-H<br>V-U | 1-Reduce pump speed with closure of the valve alternatively and gradually till pump reaches the patient blood speed with the value closed.<br>2-Put pump off.<br>3-As before | 4-As before.<br>5-Reduce pump F speed and put it on till saline reaches the air detector. Then open the recirculation Segment gradually & suck the contents into filter segments.<br>6-As before |

4—How to Get Use of the Lines

The accelerated hemodialysis lines are manufactured in the same way and with different standard types & sizes according to the used Hemodialysis machines & the weight of the patient.

An additional recirculation segment connected to the venous line distal to the air detector & the arterial line proximal to the pump segment with two T shaped connections will change the line into a recirculation line A short segment of few centimeters is sufficient.

1—Using the Lines for Accelerated Hemodialysis

High filter blood flow dialysis allows,

Heparin free dialysis.
Increase the ultrafilteration
Using bigger filters with higher efficiency.

Low patient blood flow allows dialysis in patients with;

low body weight.
inefficient A-V fistula.
Cardiovascular instability.

High filter—Low patient blood flow dialysis;

Allows a combination of both benefits.

2—Using the Lines in Double Needle Hemodialysis

The accelerated hemodialysis lines can perform conventional double needle hemodialysis by closing the acceleration segment.

The acceleration segment can be opened & the patient lines closed temporarily to allow adjustment of the fistula needles if needed. this will give the lines an additional benefit over the traditional double needle lines.

CONCLUSION

Due to the universal benefit of the accelerated hemodialysis lines in both accelerated hemodialysis & double needle hemodialysis, the low coast of the lines & the manual valves & the reuse of the automated valves, it is recommended to replace the traditional double needle lines with the pump controlled or pressure controlled hemodialysis lines with the proper calibrated recirculation valves.

II—The Regulator of Accelerated Hemodialysis Lines

In the pump controlled Accelerated Hemodialysis Lines the additional pump regulates the blood flow in the lines.

In the valve controlled Accelerated Hemodialysis lines the regulators of blood flow may be divided according to the sensor of the regulator into;

A—The calibrated recirculation valve (pressure sensor).

B—The Doppler flow meter controlled valve system (flow sensor).

A—The Calibrated Recirculation Valve

1—The Algebraic Principle of the Recirculation Valve (FIG. 2).

The Flow of any fluid through a resistance in a tube is equal to the square root of the pressure gradient across the constriction multiplied by a constant.

$$F = C\sqrt{\Delta p} \qquad (1)$$

The factors that affect this constant include fluid related factors as viscosity & temperature & line related factors including the diameter of the lines & shape & diameter of the orifice.

In the pressure controlled accelerated hemodialysis lines the pressure gradient across the patient & the pressing segment is equal to the difference between the arterial & venous lines pressure.

$$\Delta p = Pv - Pa \qquad (2)$$

The filter blood flow is equal to the sum of the patient and the recirculation blood flow.

$$Ff = Fp + Fr \qquad (3)$$

The blood flow rate in the recirculation segment is equal to the recirculation segment constant multiplied by the square root of the pressure gradient.

$$Fr = Cr\sqrt{Pv - Pa} \qquad (4)$$

Conclusion from equation (4) Cr can be experimentally calculated from equation (4) while the patient line is closed. It will vary in the Accelerated hemodialysis line s according to changes in the orifice shape & diameter (degree of valve closure) & blood viscosity (mainly determined by hematocrit value). Thus for each particular line the relation between the degree of valve closure, Hematocrite (An important variable in patients with renal failure) & Cr can be drawn in graphs. These graphs can help to guide for the proper degree of valve closure to achieve the target Cr.

The blood flow rate in the patient segment is equal to the patient constant multiplied by the square root of the pressure gradient. This fact is true whether the recirculation line is close (Double needle hemodialysis) or open (Accelerated hemodialysis)

$$Fp=Cp\ Pv-Pa \quad (5)$$

Conclusion From equation (5) Cp can be experimentally calculated from Fp & (Pv−Pa) while the recirculation line is closed (Double needle hemodialysis). The algebraic calculation of Cp is very complex due to multiplicity of the tube system in the patient lines [Venous line—Venous fistula needle—Recipient vein—venous system—Heart pump—Arterial system—Donor Artery—Arterial fistula needle—Arterial line. It will be constant for the same patient in the same session so long the vascular resistance is maintained constant.

Conclusion From equation (5) The patient blood flow in the accelerated hemodialysis lines can be restored if The pressure gradient that is achieved while the recirculation segment is closed (Double needle hemodialysis) is restored while the recirculation line is open (Accelerated hemodialysis).

From equations 3,4,5 the ratio of the patient/recirculation segment blood flow is equal to the ratio of the patient/recirculation constants.

$$Fp/Fr=Cp/Cr \quad (6)$$

Conclusion From equation (6) Cr can be calculated if Fp/Fr & Cp are known.

2—The Structure of the Calibrated Recirculation Valves

Different types of calibrated recirculation valves can be manufactured. According to:

1—Technique of Operation

Manually operated valves:
  The self calibrated valve.
  The graduated valve with separate graphs & tables.

Automatic valves:
  The inbuilt program in the hemodialysis machine.
  The program in a separate computer.

2—Mode of Control of the Compressing Segment
The graduated valve (Manual or automatic)
The precalibrated valve (Manual or automatic)

Figure 3:
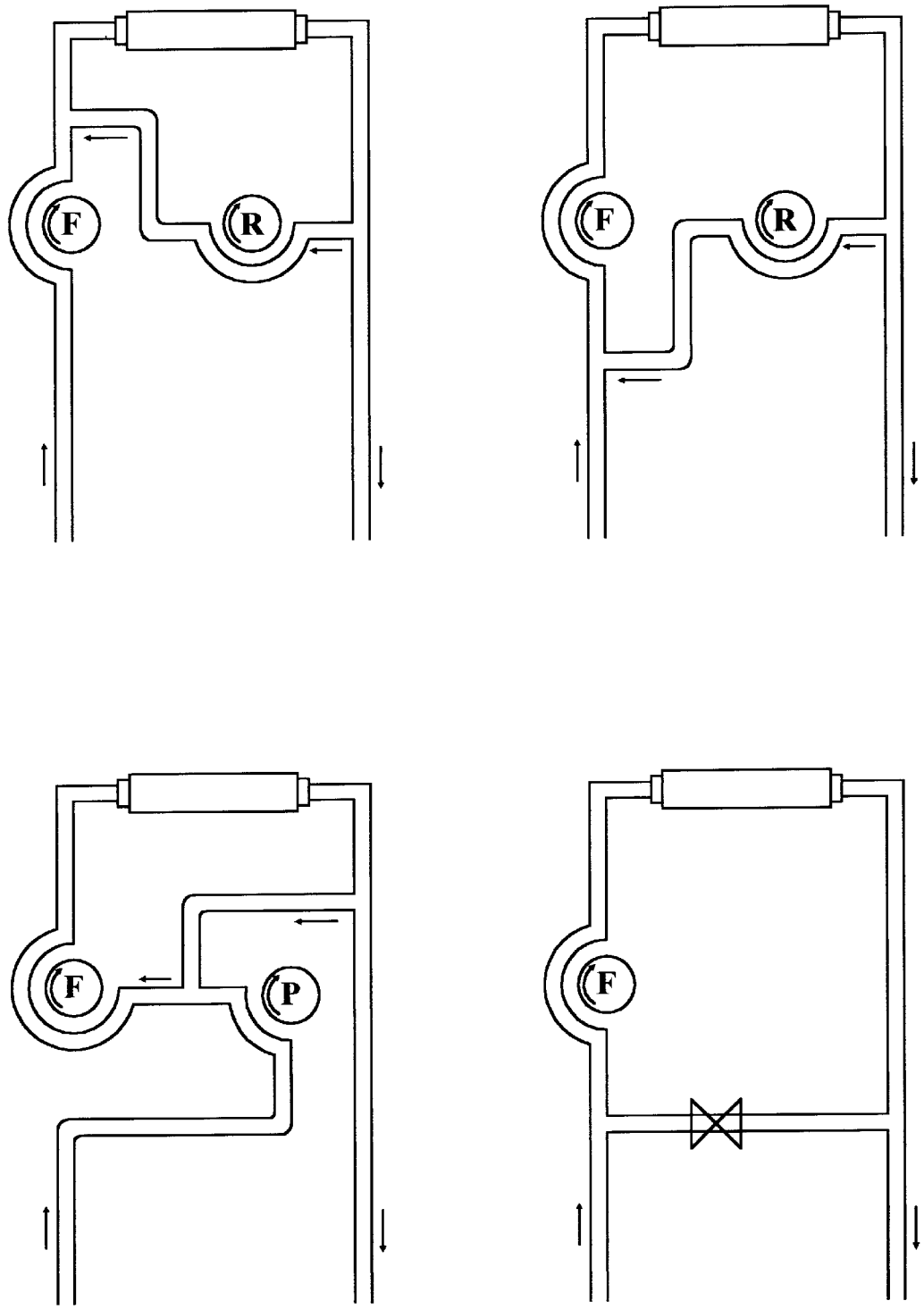
FIG. 3: Different models of Acceleration hemodialysis lines connected to the hemodialysis machine; A; model (M-H-RP) B; models (M-H-AF), (M-U-R) C; models (M-H-PF), (M-U-P) D; models (V-H), (V-U).
Figure 4:
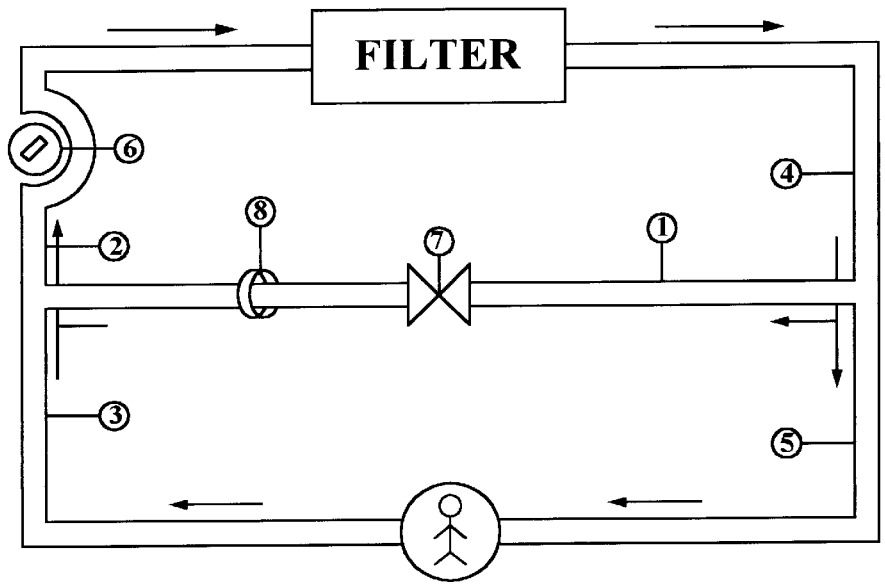
FIG. 4; The pressure controlled accelerated hemodialysis circuit; the recirculation segment (1), the filter segment of the arterial line (2), the patient segment of the arterial line (3),the filter segment of the venous line (4) & the patient segment of the venous line (5), the blood pump (6) & the valve(7) the recirculation segment clamp (8).

3—Structure of the Compressing or Obstructing Segment (FIG. 3) e.g.
A—Straight triangular hole.
B—Sickle shaped hole.
C—Tooth.
D—External Screw.
E—Running wheel.
F—kinking lines.
G—Internal screw
H—Rotating hole 1—The Precalibrated Manual Valve (with Sickle Shaped Hole Compressing Segment). (FIG. 4)

It is a manual valve that has a graduation of a linear relation between Fp/Ff & (Pv−Pa) on one hand & Fp/Ff & the created change on the recirculation segment diameter Dr on the other hand For simplicity the hematocrit level was not included.

The valve is formed of;

1—The Valve Tube (7)
A hard tube of internal diameter equal to the external diameter of the recirculation segment (1).
In the region facing the pressing disc (8) the inner two thirds of its wall is missing This defect allows uninterrupted obstruction of the recirculation segment by the pressing disc.

2—The Upper Plate (9)
A perpendicular hard plate attached to the upper part of the valve tube behind the circular plate (12) and protruding beyond it to form the first arrow (10).

3—The Lower Plate (11)
A perpendicular hard plate connecting the valve tube to the sheath of the axis (23) behind the circular plate & in front of the pressing disc.

4—The Circular Plate (12)
A circular plate with a peripheral calibrated graduation of the pressure gradient with an arrow; arrow 2 (14) at its zero reading that points to the ratio of the patient/filter blood flow drawn on the pressing disc.
The plate has a central hole (15) through which the axis passes to allow rotation of the plate.
The plate has a C shaped hole (16) occupying half of its surface to allow its free movement around the valve tube (7).

5—The Pressing Disc (18)
A hard disc with a peripheral calibration of the ratio of patient/filter blood flow rates. The set point of this line is the ratio of the patient/filter blood flow rate that will be achieved with the valve completely opened (minimal valve resistance) & the patient & filter lines are directly connected (minimal patient resistance) This set point is a measure of relative resistance of the recirculation & patient segments.
The disc has a central hole (19) through which the axis passes to allow rotation of the disc.
The disc has a sickle shaped hole (20) through which the valve tube passes. The wide end of the hole exerts no pressure on the recirculation segment while the narrow end occludes the segment completely.
After adjustment of the circular plate, arrow 2 will point to the ratio of patient/filter blood flow achieved by the compression effect of the pressing disc. This graduation will be specific for this particular line and valve.
The disc has 2 perpendicular anterior shoulders (21) to facilitate its rotation over the recirculation segment.

6—The Central Axis (22)
An axis which passes through the central hole of both the circular plate (15) and the pressing disc (19).
At the posterior part of the axis behind the graduated plate & at the anterior part in front of the pressing disc, the axis has a sheath (23) This sheath is attached to the valve tube anteriorly & posteriorly by the lower plate (11).
The anterior & posterior parts of the axis sheath, the circular plate and the disc are fixed around the axis between the two screws, the anterior screw (24) & the posterior screw (25).

Figure 5:
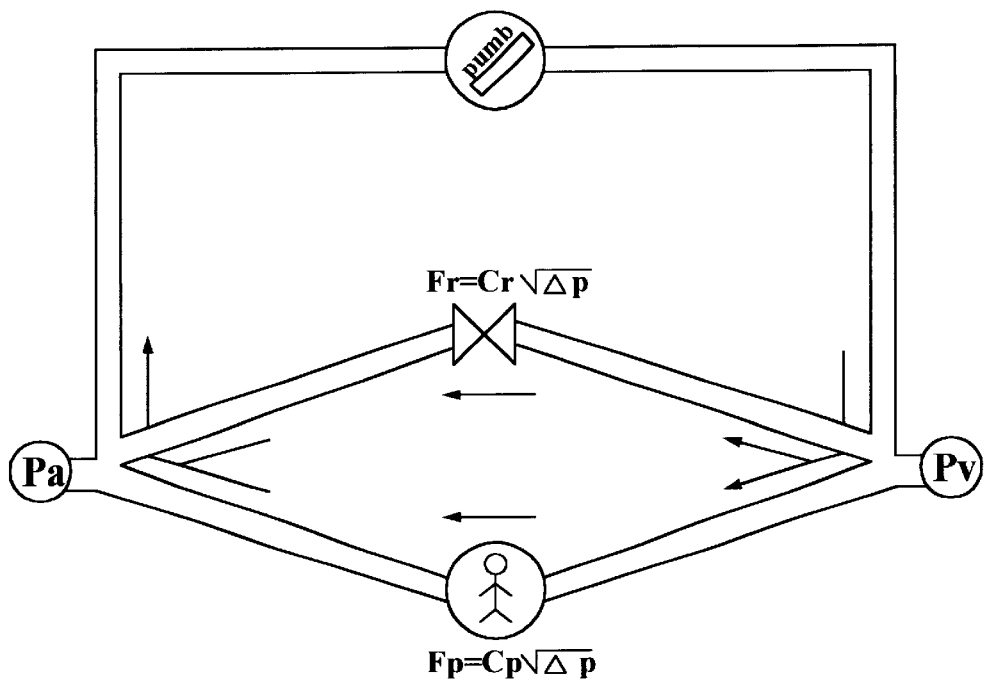
FIG. 5; The algebraic relation between different blood flow rates and flow ratios & between the diameter of the recirculation line and the pressure(s) in the arterial & venous lines; Fr=flow rate in the recirculation line Ff=the filter blood flow rate Fp=the patient blood flow rate Fp/Ff=the ratio of patient to filter blood flow rates Cp=Patient constant Cr=Recirculation segment constant Pa=pressure in the patient segment of the arterial line Pv=pressure of the patient segment of the venous line.

2—The Precalibrated Manual Valve with Separate Graphs & Tables (FIG. 5)
This valve is formed of;
1—A compressing or obstructing segment of any of the types shown in figure The valve will have known graduations matching its corresponding compression effect (0=closed, 10=completely opened).

2—Graphs & tables showing the relation of the following three parameters

The set point pressure gradient Δp of the patient as an index of Cp.

The degree of closure of the valve & corresponding recirculation diameter (Dr) & the hematocrite (Ht) of the patient as an index of Cr.

The target ratio of patient/filter blood flow rates (fp/ff).

Figure 6:
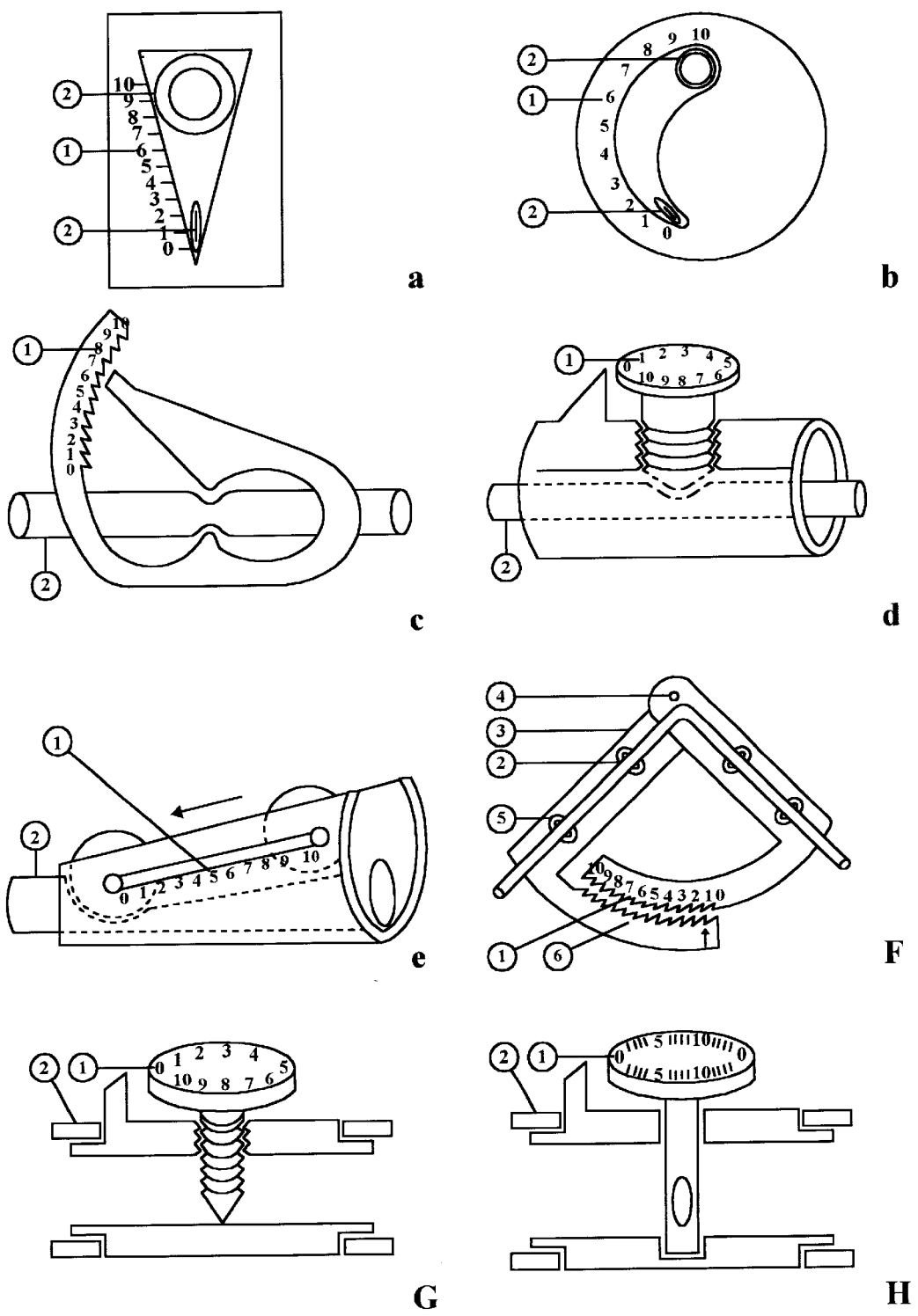
FIG. 6; structure of different forms of the compressing or obstructing portion of the valve: Forms A—straight triangular hole B—sickle shaped hole C—tooth D—external screw E—running wheel E—kinking lines. F—Internal screw G—Rotating hole. Structure Each valve has 11 graduation (1) showing the degree of closure of the valve corresponding to its effect on the diameter of the recirculation segment (2)(0=closed, 1=10% of full open diameter, 2=20% of full open diameter . . . , 10=fully open). The kinking line valve has 2 limbs (3) with a central joint (4) & clips (5) on its anterior surface to fix the line. The graduation (2) is drawn on the anterior surface of 2 toothed semicircular hands (6) which move against each other to fix the joint at the target position.

3—The precalibrated & graduated automatic recirculation valves with inbuilt computer program in the hemodialysis machine (with kinking line compression segment). (FIG. 6).

The hemodialysis machine (8) will adjust the target filter blood flow Ff by adjusting the pump speed as usual & will detect the arterial & venous lines pressures.

A soft or hard ware program (9) added to the hemodialysis machine & supplied with different tables & graphs showing the relation of the three prementioned parameters for each type of Accelerated hemodialysis line in the market.

The program automatically adjusts the valve to achieve the suitable change in the recirculation segment diameter to achieve the target patient blood flow.

The automatic kinking line compressing part of the valve is formed of; An electric motor (11), An arm (12) to transfer motion from the motor to the joint of the acceleration line holder. Acceleration line holder formed of 2 limbs with a central joint (13).

Figure 7:
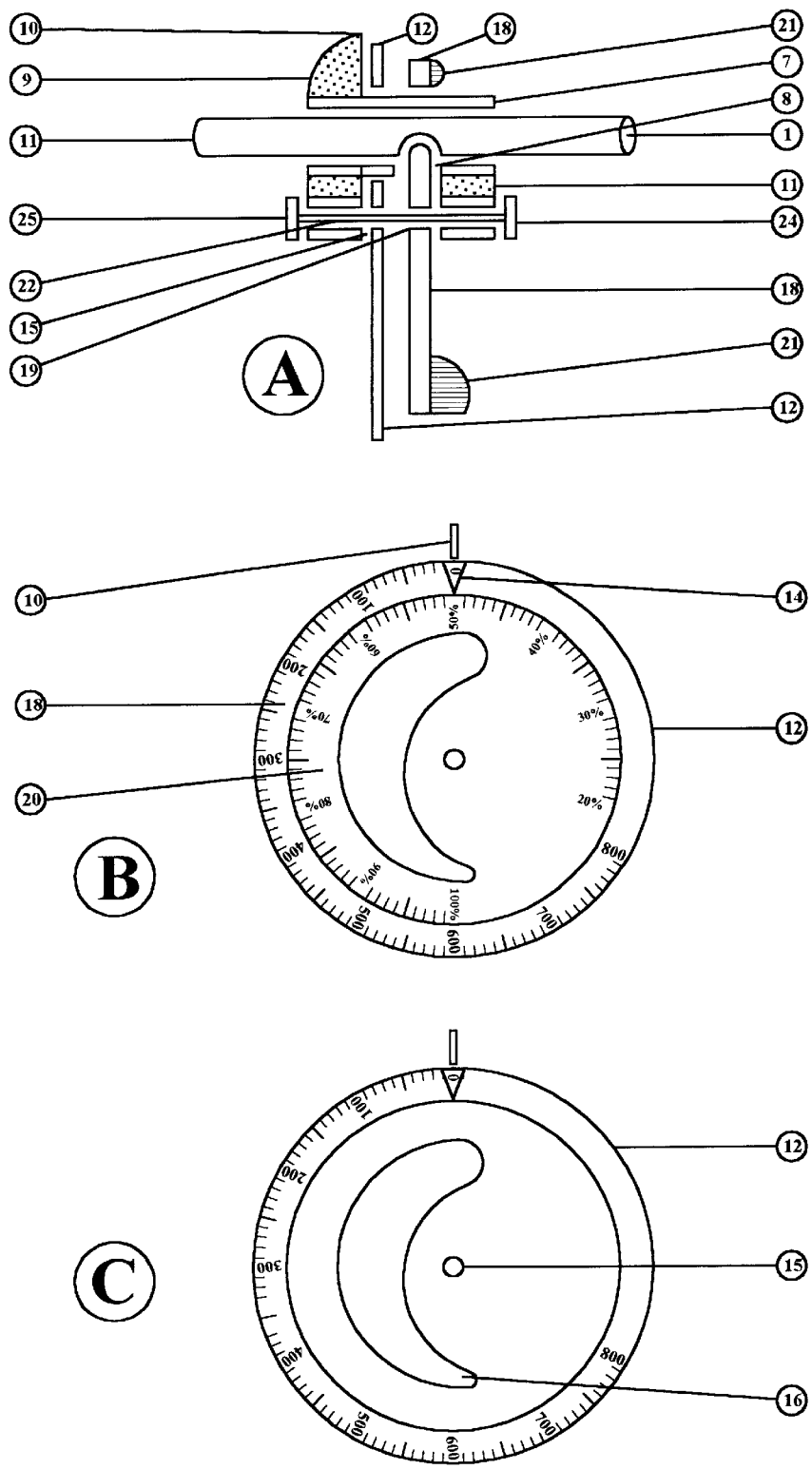
FIG. 7; The structure of the Calibrated valve A—Lateral view B—Anterior view C—The circular plate the valve tube (7) the missing segment of the valve tube (8) the upper plate (9) the first arrow (10) the lower plate (11) the circular plate

4—The Precalibrated & Graduated Automatic Recirculation Valves with Separate Computer Program (with Linking Line Compression Segment). (FIG. 7)

The hemodialysis machine (4) will adjust the target filter blood flow by adjusting the pump speed as usual & will detect the arterial & venous lines pressures.

The computer program will be added to a separate computer (5) & supplied with different tables & graphs showing the relation of the three prementioned parameters for each type of Accelerated hemodialysis lines in the market.

The computer will be supplied with the type of lines used, the target filter & patient blood flow rates & the actual arterial & venous lines pressures & the valve will be automatically adjusted to achieve the suitable change in the recirculation segment diameter to achieve the target patient blood flow.

3—How to Use the Calibrated Recirculation Valves to Perform an Accelerated Hemodialysis Session?

1—The Accelerated Hemodialysis Order

Decide the target filter & Patient blood flow (Ff), (FP), High filter blood flow dialysis allows; Heparin free dialysis, Increase the ultafilteration or Using bigger filters with higher efficiency. Low patient bloodflow allows dialysis in patients with; low body weight, inefficient A-V fistula or Cardiovascular instability.

The amount of hemodialysis therapy (time and frequency) can be calculated as usual.

The filter blood flow (Ff) will be achieved by setting the pump speed & The patient blood flow (FP) can be achieved by adjusting the patient/filter blood flow ratio by the calibrated valve.

The arterial and venous line pressures (Pa), (Pv) will be shown by the pressure monitors of the hemodialysis machines.

2—Adjusting the Valve

2—a Adjusting the Self Calibrated Valve (FIG. 8)

1—Identify the Set Point Fp/Ff of the Lines

Open the valve completely.

Rotate the circular plate so that arrow 1 faces the zero grade of the circular plate.

Arrow 2 which corresponds to this zero grade will point to the set point Fp/Ff of the lines on the pressing disc.

2—Identify the Set Point Δp of the Patient

Close the recirculation clamp.

Adjust Pf to a preset value of 100 ml/min in children or 200 ml/min in adults.

Measure Δp from the equation (Δp=Pv−Pa)

3—Adjust the Set Point Δp of the Patient at the Circular Plate

Rotate the circular plate so that the arrow 1 (which identifies the recirculation line) points to the set point Δp of the patient.

Arrow 2 will point to the Fp/Ff ratio that will be achieved if the recirculation clamp is opened.

4—Adjust the Filter Blood Flow

Open the recirculation clamp.

Increase the pump speed to the target Ff.

5—Adjust the Pressing Disc to Achieve Target Fp/Ff Ratio

Rotate the pressing disc so that the required patient/filter blood flow ratio marked on the pressing scale faces Arrow 2. at its new position.

At this point the sickle hole will compress the recirculation segment to achieve the target recirculation segment diameter Dr.

6—Regular Check Up of the Working Pressure Gradient

Repeat the previous steps (2–6) to readjust the valve if the pressure gradient Δp changes during the session.

2—b Adjusting the Graduated Valve with Separate Graphs & Figures

Identify the set point Δp of the patient as mentioned before.

Use the appropriate graphs for the type of the lines used to identify the proper valve adjustment to achieve the target Fp/Ff ratio.

Open the recirculation segment clamp & adjust the pump speed to the target Ff

Adjust the valve manually to achieve the target Fp/Ff ratio.

Repeat the previous steps to readjust the valve if the working pressure gradient Δp changes during the session.

2—c Adjusting the Automatic Graduated Recirculation Valve with Inbuilt Computer Program in the Hemodialysis Machine Feed the soft ware program with the desired filter & patient blood flows.

The program will adjust the graduated automatic pressing segment in the following steps.

1—Close the recirculation line.

2—Adjust the pump speed to the target Fp

3—Detect Pv & Pa

4—Calculate & memorize Pv−Pa at this target Fp

5—Open the recirculation valve completely (aiming to save the patient from exposure to undesired high blood flow rate).

6—Adjust the pump speed to the target Ff

7—Gradually open the valve till the memorized Pv−Pa is restored.

8—Continuous monitoring of the memorized target Pv−Pa & fine readjustment of the valve accordingly within the accepted Pv−Pa range noting that the pressure alarms will work uninterruptedly as usual for unaccepted Pv or Pa values.

2—d Adjusting the Automatic Calibrated Recirculation Valve with Inbuilt Computer Program in the Hemodialysis Machine Feed the soft ware program with the type of the lines used, the hematocrite value of the patient and the desired filter & patient blood flows.

The program will adjust the calibrated automatic pressing segment in the following steps:
1—Close the recirculation line.
2—Adjust the pump speed to the target Fp
3—Detect Pv & Pa
4—Calculate & memorize Cp from equation 5
5—Calculate & memorize the target Cr from the equation 6
6—Calculate & memorize the target Dr from Cr.
7—Adjust Dr (the degree of valve closure) according to the filed data of Hematocrite (index of viscosity) & type of the line (lines diameter & shape of the orifice).

In the automatic kinking line valve the direction & intensity of the electric current derived to the motor of the valve will control the degree of bending of the acceleration line. Each degree of bending of the line will achieve a pretested change of the valve diameter.

After the session the lines will be removed from the valve which will be used in the subsequent sessions.

2—e Adjusting the Automatic Graduated Recirculation Valve with Separate Computer Program The operator (nurses or doctors) will do the following:
1—Close the recirculation line.
2—Adjust the pump speed to the target Fp
3—Detect Pv & Pa
4—Calculate & Pv–Pa at this target Fp.
5—Feed the program with the target, Ff, Fp & Pv–Pa at this target Fp.

The program will do the following:
1—Open the recirculation valve completely (aiming to save the patient from exposure to undesired high blood flow rate).
2—Inform the operator to adjust the pump speed to the target Ff
3—Gradually close the valve till the memorized Pv–Pa is restored.
4—Continuos monitoring of the memorized target Pv–Pa & fine readjustment of the valve accordingly, noting that the pressure alarms of the hemodialysis machine will work uninterruptedly as usual for unaccepted Pv or Pa values.

In the automatic kinking line valve the direction & intensity of the electric current derived to the motor of the valve will control the degree of bending of the acceleration line. Each degree of bending of the line will achieve a predetermined change of the recirculation segment diameter.

2—f Adjusting the Automatic Calibrated Recirculation Valve with Separate Computer Program The operator will do the following:
1—Close the recirculation line.
2—Adjust the pump speed to the target Fp
3—Detect Pv & Pa at this target Fp
4—Feed the soft ware program with the type of the lines used the hematocrite value of the patient and the target Ff, Fp & Pv & Pa at this target Fp.

The program will adjust the calibrated automatic pressing segment in the following steps:
1—Calculate & memorize Cp from equation 5
2—Calculate & memorize the target Cr from the equation 6
3—Calculate target Dr (the degree of valve closure) from target according to the filed data of Hematocrite (index of viscosity) & type of line (lines diameter & shape of the orifice).
4'Open the recirculation valve completely (aiming to save the patient from exposure to undesired high blood flow rate).
5—Inform the operator to adjust the pump speed to the target Ff
6—Gradually close the valve till the target Dr is acheived.
7—Continuos monitoring of the memorized target Pv–Pa & fine readjustment of the valve accordingly, noting that the pressure alarms of the hemodialysis machine will work uninterruptedly as usual.

4—How to get Use of the Valve?
The valves will be manufactured & calibrated mathematically and the calibration will be checked experimentally as described.
The calibration will be shown on the circular plate & on the compressing disc in the self calibrated valve supplied as separate tables or graphs in the graduated valves or inserted in the computer program in the automatic valves.
One of the forementioned types of the calibrated valves will be used with the lines.

B—The Doppler Flow Meter Controlled Valve System

1—Definition
An optional system used in valve controlled accelerated hemodialysis lines (V) lines to regulate blood flow in the acceleration line and consequently in the patient lines by direct measurement of the blood flow rate in the acceleration segment or the patient segment of the arterial or venous line.

2—Components of the System: (FIG. 12)
Doppler Transducer (1) to measure blood flow rate in the arterial line of the patient
Control unit (2) to receive signals from the transducer and regulate the valve.
A valve to regulate blood flow in the acceleration line composed of;
(A)—An electric motor (3).
(B)—An arm (4) to transfer motion from the motor to the joint of the acceleration line holder.
(c)—Recirculation segment holder formed of 2 limbs (4) with a central joint (5)

3—How to Use the System?
Use the transducer for direct measurement of the blood flow rate in the acceleration segment or the patient segment of the arterial or venous line.
Hold the recirculation segment to the limbs of the valve which make the line open if the limbs are straight and close with decrease in the angle between the 2 limbs.
Adjust the upper and lower limits of blood flow through the arterial line of the patient.
(a) If blood flow through the patient segment of the arterial line exceeds the upper limit, the control unit will put on the motor so as to push the motion arm to increase the angle between the two limbs holding the acceleration line and thus the valve will open and blood flow will decrease through the recirculation segment and increase through the arterial line of the patient.
(b) If blood flow through the arterial line of the patient is below the lower limit the control unit will reverse the direction of the electrical current and the motor will pull the motion arm to decrease the arm's angle and thus the valve will close and the blood flow will decrease though the recirculation segment and increase though the arterial line of the patient.
(c) If blood flow through the arterial line of the patient is within the accepted range the control unit will put off the electrical current and thus will maintain the same blood flow through the recirculation segment & the patient blood flow.

N.B.

The Patient blood flow (pump p) or (pump F-R) speed should not exceed the patient tolerance.

The filter dlood speed should not exceed the filter tolerance as specified by the manufacturing Company.

Neither the Patient no the Recirculation pump speed should exceed the filter pump speed (F>R) (F>P). Hemodialysis machines having acceleration hemodialysis Safety program will alarm if (F<R)(F<p).

III—The Accelerated Hemodialysis Safety Program

The safety program aims to avoid errors in the Accelerate Hemodialysis order concerning A—The 2 pump speed order relative to each other in the Motor controlled lines.

B—The Ultrafilterarion relative to the patient blood flow order.

A—The Blood Flow Rate Safety Program (FIG. 13)

It is an optional computer program used with hemodialysis machines used for accelerated hemodialysis using type (M) accelerated hemodialysis lines It aims to:

1—Putting on the additional pump (acceleration or patient segment of arterial line pump) in continues motion, in contrast to the single needle hemodialysis where the additional pump works inerruptedly.

2—In models (M-H-RF), (M-U-R), giving an alarm if;
the speed of the additional pump (recirculation segment pump R) exceeds the speed of the main pump (filter segment of the arterial line pump F) [R>F]
to avoid passage of blood in the patient in the reverse direction with the possibility of internal recirculation.

$$Ff=Fp+Fr \quad (3)$$

If Fr>Ff→Fp=−ve

3—In models (M-H-PF), (M-U-P) giving an alarm if
The speed of the additional pump (the patient segment of arterial line P) exceeds The speed of the main pump (filter segment of the arterial line pump F) [P>F]
to avoid passage of blood in the recirculation segment in the reverse direction with non beneficial external recirculation $$Ff=Fp+Fr \quad (3)$$

Fp>Ff→Fr=−ve

B—The Ultrafilteration Rate Safety Program

This program gives an alarm if the ultrafilteration goal is more than capacity of the actual patient blood flow [Speed of pump (p) or speed of pumps (F–A)]. To avoid hemoconcentation with higher possibility of blood clotting in the filter.

What is claimed is:

1. A system for extracorporeal blood treatment with a high blood flow rate through the filter and a low blood flow to and from the patient comprising an extracorporeal blood path comprising 1) Arterial line connecting blood from the patient to the filter with a side line to inject anticoagulant and a suitable segment to fit for the blood pump of the hemodialysis machine situated between the filter and its junction with the recirculation line and an optional suitable segment to fit for a second blood pump of the hemodialysis machine situated between the patient and its junction with the acceleration line, 2) Venous line connecting blood from the filter to the patient with an air trapping chamber, and 3) recirculation line carrying part of the blood from the venous line to the arterial line with an optional adjustable valve or an optional suitable segment to fit for a second blood pump of the hemodialysis machine, Where 3 different blood flow rates 1) blood flow rate to the filter in the blood circuit equal to the sum of 2) the blood flow rate in the recirculation line and 3) the blood flow rate to and from the patient, are generated and adjusted in the circuit by either, 1) two blood pumps situated at two of the 3 sites,
   a) the arterial line between the filter and its connection with the recirculation line,
   b) the arterial line between the patient and its connection with the recirculation line or
   c) the recirculation line, or 2) one blood pump and one valve, where
   a) the blood pump is situated at the arterial line between the filter and its connection with the recirculation line and
   b) the valve at the recirculation line.

2. As in claim 1 the valve on the recirculation line can adjust the target blood flow rate in the recirculation line by adjusting its resistance and hence the pressure gradient across it either 1) Manually or 2) Automatically, according to the blood flow rate revealed directly by a Doppler flow sensor or calculated according to preset calibration data concerning, 1) length and caliber of the lines, 2) pressure in the arterial lines 3) pressure in the venous lines 4) blood hematocrite and viscosity, derived directly from the hemodialysis machine or fed by the operator and interpreted by, 1) special graphs and tables 2) a computerized program in a separate computer 3) a computerized program inbuilt in the hemodialysis machine.

3. As in claim 1 a safety program will be fed by the blood flow rate to and from the patient and through the filter and the ultrafilteration rate and alert the operator if he a) selected low patient blood flow and a relatively high ultrafilteration rate, to avoid hemoconcentration and hypercoagulability of the blood in the filter or b) selected patient blood flow to and from the patient higher than filter blood flow, to avoid reversal of the direction of the blood flow in the recirculation line from the arterial line to the venous line and creation of a closed circuit from and to the patient bypassing the filter.

* * * * *